United States Patent [19]

Tschaen et al.

[11] Patent Number: 5,124,448
[45] Date of Patent: Jun. 23, 1992

[54] DEBLOCKING PROCESS FOR ALLYL ESTERS WITH REGENERATABLE POLYMER SUPPORTED PD(O)

[75] Inventors: David M. Tschaen, Aberdeen; F. Edward Roberts, Princeton; Thomas R. Verhoeven, Cranford, all of N.J.

[73] Assignee: Merck & Co., Inc., Rahway, N.J.

[21] Appl. No.: 610,711

[22] Filed: Nov. 7, 1990

Related U.S. Application Data

[63] Continuation of Ser. No. 481,759, Feb. 15, 1990, abandoned, which is a continuation of Ser. No. 314,625, Feb. 23, 1989, abandoned.

[51] Int. Cl.$^5$ .................. C07D 501/04; C07D 499/04
[52] U.S. Cl. .................................... 540/221; 540/222; 540/310; 540/350
[58] Field of Search ............... 540/350, 221, 310, 222

[56] References Cited

U.S. PATENT DOCUMENTS 4,314,942  2/1982  McCombie .................. 260/245.2

OTHER PUBLICATIONS

Clark et al., J. Am. Chem. Soc. vol. 100, pp. 7779-7781 (1978).
Jeffrey et al., J. Org. Chem., vol. 47, pp. 587-590 (1982).

Primary Examiner—Nicholas S. Rizzo
Attorney, Agent, or Firm—John W. Harbour; Hesna J. Pfeiffer

[57] ABSTRACT

A regeneratable polymer-supported Pd(O) catalytic deblocking process using a regeneratable polymer-supported Pd(O) catalyst in a biphasic system deblocks various allyl-protected ester, carbonates, carbamates and cinnamyl esters.

12 Claims, No Drawings

DEBLOCKING PROCESS FOR ALLYL ESTERS WITH REGENERATABLE POLYMER SUPPORTED PD(O)

This is a continuation of application Ser. No. 07/481,759, filed Feb. 15, 1990, now abandoned, which is a continuation of application Ser. No. 314,625, filed Feb. 23, 1989, now abandoned.

BACKGROUND OF THE INVENTION

Protecting groups in the synthesis of a wide variety of organic compounds, particularly antibiotics and oligopeptides, are essential to prevent unwanted reactions of side groups at various intermediate steps. The useful qualities of a protecting group depend upon the mildness of conditions required for its removal.

Allyl protecting groups on esters, carbonates, carbamates or cinnamyl esters can normally be removed by palladium, particularly organic soluble palladium complexes possessing a coordinating phosphine ligand. See, for example, U.S. Pat. No. 4,314,942; its corresponding EPO application with publication number 0013663; Trost. B. M. et al., *J. Am. Chem. Soc.*, 100, 7779 (1978); and Jeffrey, P. D. et al., *J. Org. Chem.*, 47, 587 (1982). However, none of these palladium-based deprotection methods provide means for regenerating polymer supported palladium.

Accordingly, a purpose of the present invention is to provide methods and means of substantially regenerating palladium in palladium-based deprotection of allyl esters, allyl carbonate, allyl carbamates and cinnamyl esters. Regeneration of palladium avoids the expense of using new batches repeatedly in the commercial production of a variety of compounds, e.g. antibiotics such as cefoxitin or imipenem. In addition, no loss of yield in deprotected compound results.

Furthermore, the methods of the present invention provide readily manipulable complexes of palladium, in the form of polymer supported Pd(O). These complexes are insoluble in both organic and aqueous environments, properties of commercial advantage in synthesis of a variety of compounds.

The methods of the present invention also provide mild conditions for synthesizing a wide variety of organic compounds, many of which are unstable and susceptible to inactivation during synthesis.

SUMMARY OF THE INVENTION

The invention is a method of deblocking a protective group by a solid-phase catalyst and simultaneously regenerating the catalyst. The method includes a one-step procedure of reacting about one equivalent of a compound having one or more protecting groups with a catalytic quantity of polymer supported Pd(O) in the presence of one or more equivalents of nucleophile. The procedure achieves simultaneous regeneration of the polymer supported Pd(O).

Suitable compounds include allyl esters, allyl carbonates, allyl carbonates and cinnamyl esters. Allyl esters are preferred.

The polymer supported Pd(O) is preferrably a complex of polystyrene bound triphenylphosphine and tetrakistriphenylphosphine in a mole-to-mole ratio of between about 30:1 and about 50:1.

Suitable nucleophiles include 1,3-cyclopentanedione, 2-methyl-1,3-cyclopentanedione, 2-methyl-1,3-cyclohexanedione, potassium 2-ethyl hexanoate and N-methylmorpholine.

The compound having one or more protecting groups is preferably cefoxitin or imipenem.

The preferred catalytic quantity of polymer supported Pd(O) is between about 30 mole % and about 0.25 mole % of the protecting group, and more preferably between about 10 mole % and about 5 mole % of the protecting group.

Within the present invention is a method of deblocking a protecting group with polymer supported Pd(O), and then regenerating the polymer supported-Pd(O), comprising the steps of:

(a) providing about an equivalent of a compound having one or more protecting groups to be removed, as cefoxitin or imipenem, the compound being dissolved in an organic non-hydroxylic solvent, and the protecting groups preferably being allyl moieties;

(b) adding about one equivalent of a nucleophile, the nucleophile preferably being selected from 1-3-cyclopentanedione, 2-methyl- 1,3-cyclopentanedione, 2-methyl-1,3-cyclohexanedione, potassium 2-ethyl hexanoate and N-methylmorpholine;

(c) mixing with about one equivalent of a polymer supported Pd(O) to yield deblocked compound and reacted supported Pd(O);

(d) separating the reacted polymer supported Pd(O) from deblocked compound, preferably by adding aqueous solution, mixing and removing the reacted polymer supported Pd(O) from the organic phase; and (e) regenerating the reacted polymer supported Pd(O) by reaction with more than one equivalent of a reducing agent, preferably $NaBH_4$, in aqueous solution.

BRIEF DESCRIPTION OF THE INVENTION

A method is disclosed for deblocking a protecting group by a solid-phase catalyst and simultaneously regenerating said catalyst, comprising the one-step procedure of reacting one equivalent of a compound having one or more protecting groups with a catalytic quantity of polymer supported Pd(0) in the presence of one or more equivalents of a nucleophile, said protecting groups selected from the group consisting of an allyl ester, allyl carbonate, allyl carbamate and cinnamyl ester, said procedure simultaneously regenerating the polymer supported Pd(0).

A second, multiple step procedure of substantially similar effect is also disclosed. This method of deblocking a protecting group with polymer supported Pd(0), and then regenerating the polymer supported Pd(0), comprises the steps of:

(a) providing an equivalent of a compound having one or more protecting groups to be removed, said compound dissolved in an organic non-hydroxylic solvent, said protecting group selected from the group consisting of an allyl ester, allyl carbonate, allyl carbamate and cinnamyl ester;

(b) adding about one equivalent of nucleophile;

(c) mixing with about an equivalent of a polymer supported Pd(0); yielding deblocked compound and reacted polymer supported Pd(0);

(d) separating the reacted polymer supported Pd(0) from deblocked compound; and (e) regenerating the reacted polymer supported Pd(0) by reaction with more than one equivalent of a reducing agent in aqueous solution.

DETAILED DESCRIPTION OF THE INVENTION

Polymer supported Pd(0), is commercially available, or it may be easily made by reaction of tetrakis (triphenyl phosphine) palladium (0) with polystyrene-bound triphenyl phosphine or with styrene-divinylbenzene copolymer. These and other suitable methods of preparing polymer supported Pd(0) for the purpose of deblocking can be found in Trost, B.M. et al., *J. Am. Chem. Soc.*, 100, 7779 (1978) and Capka, M. et al., *Coll. Czech. Chem. Comma.*, 38, 1242 (1973). The preferred polymer supported Pd(0) is made by reacting tetrakis (triphenylphosphine) palladium (0) with polystyrene bound triphenyl phosphine, which product is sometimes hereinafter referred to as P-Pd(0).

EXAMPLE 1

Preparation of Polymer Supported Palladium

A. First Method

Following the method of Trost et al., *J. Am. Chem. Soc.*, 100, 7779 (1978), 10 g of polystyrene bound triphenylphosphine (Fluka) and 0.5 g tetrakis (triphenylphosphine) palladium(0) (Aldrich) in 50 ml of benzene was refluxed for 4 hours. The mixture was cooled to room temperature, filtered and washed with 300 ml of degassed dichloromethane. The catalyst was dried in vacuo. Atomic adsorption spectroscopy showed 0.69 mole % Pd and mole 9.5 mole % phosphate.

B. Second Method

Polystyrene bound triphenyl phosphine (Fluka, 500 mg) was placed in 15 ml deoxygenated benzene. Thereafter, 100 mg tetrakistriphenylphosphine (Aldrich) was added. After refluxing 3.5 hours, the resin was filtered, then washed with 35 ml deoxygenated methylene chloride, and dried in vacuo. Yield: 520 mg of orange-red resin. The mother liquor was concentrated in vacuo to yield 90 mg of an off-white solid.

EXAMPLE 2

Catalytic Deblocking of Imipenem Allyl Ester

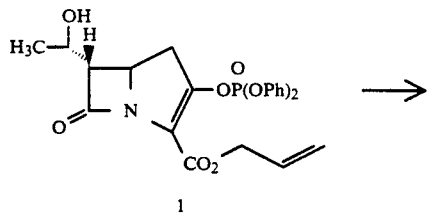

1

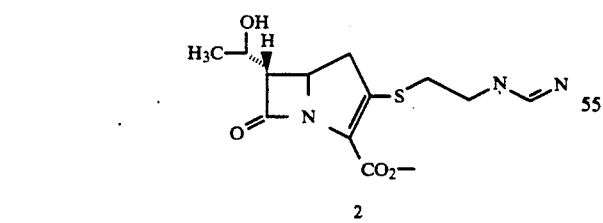

2

To a solution of 0.2 g (0.4 mmole) of compound 1 in 3 ml of N-ethylpyrolidinone at −30° C. was added 0.09 ml (0.49 mmole) of diisopropylethylamine. A solution of 0.051 g (0.045 mmole) of cysteamine hydrochloride in 3 ml of N-ethylpyrolidinone was added dropwise (15 minutes) and the mixture was stirred at −30° C. for an additional 1.25 hour. The reaction mixture was warmed to −10° C. and 0.09 ml (0.47 mmole) of diisopropylethylamine was added along with 0.089 g (0.047 mmole) of benzyformimidate hydrochloride. After 1 hour at −10° C. 8 ml of dichloromethane, 8 ml of water, 0.062 g (0.049 mmole) of 2-methyl-1,3-cyclohexanedione and 0.250 g of polymer supported palladium P-Pd(0) was added. Analysis by liquid chromatography after 1 hour shows no ester remaining. The mixture was filtered and the resin washed with 50 ml of water. After separation of the phases, liquid chromatography assay of the aqueous phase showed 63% yield (based on enol phosphate) of imipenem, compound 2.

Substitution of palladium tetrakistriphenylphosphine for polymer supported palladium leads to a 69% overall yield.

EXAMPLE 3

Catalytic Deblocking of Cefoxitin Allyl Ester

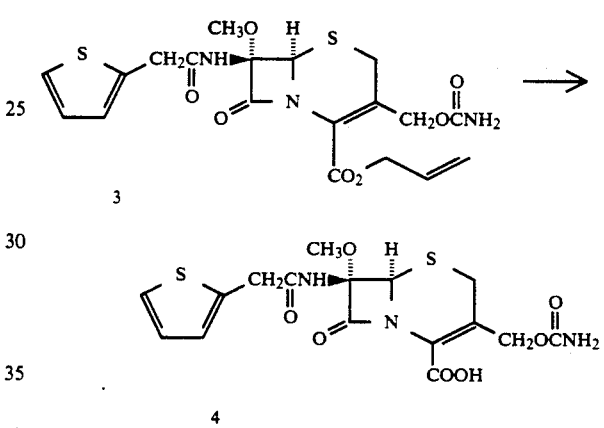

Cefoxitin allyl ester was formed by combining lithium salt of cefoxitin and allyl bromide. To a solution of 0.1 g (0.2 mmole) of cefoxitin allyl ester 3 in 5 ml of dichloromethane was added 0.032 g (0.25 mmole) of 2-methyl-1,3-cyclohexadione and 5 ml of water. The pH was adjusted to 6.25 using 1M sodium bicarbonate and the polymer supported palladium (0.330 g) was added. After 15 minutes, liquid chromatography analysis indicated no ester remaining and the mixture was filtered. The aqueous phase was separated and washed with dichloromethane. Liquid chromatography assay of the aqueous phase indicated an 83% yield of cefoxitin, 4.

EXAMPLE 4

Stoichiometric Deblocking of Imipenem Allyl Ester

The procedure of Example 2 is repeated, except that 4.90 g (one equivalent) of P-Pd(0) is used instead of 0.250 g. Reacted P-Pd(0) is regenerated by treatment in $H_2O$/THF with excess (10-equiv.) sodium borohydride.

EXAMPLE 5

Stoichiometric Deblocking of Cefoxitin Allyl Ester

The procedure of Example 3 is repeated, except that 3.30 g (one equivalent) of P-Pd(0) is used instead of 0.330 g. Reacted P-Pd(0) is regenerated by treatment in $H_2O$/THF with excess (10 equiv.) sodium borohydride.

EXAMPLE 6

Catalytic Deblocking of Allyl Carbamates

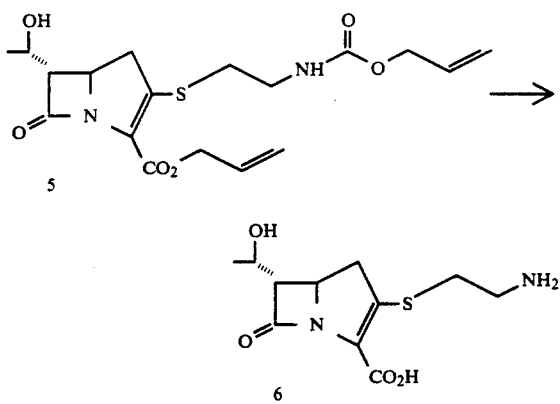

A. Bisprotected 5 (96 mg, 0.24 mmoles) was dissolved in 5 ml $CH_2Cl_2$ and 5 ml of 0.5M N-methylmorpholine HCl (pH 6.85). A quantity of 280 mg (0.24 mmoles) of $Pd(PPh_3)_4$ was added, then after twenty minutes another 280 mg was added. The reaction was stirred at room temperature for 1 hour. A resulting yellow precipitate was filtered and washed with 50 ml of 0.5M N-methylmorpholine HCl (pH 6.85), yielding compound 6. 25% yield by liquid chromatography.

B. The procedure of Example 6A, supra, is repeated, except that 480 mg of P-Pd(0) is employed instead of $Pd(PPh_3)_4$. Catalytic deblocking of both allyl groups of 5 occurs.

While the foregoing specification teaches the principles of the present invention, with examples provided for the purposes of illustration, it will be understood that the practice of the invention encompasses all of the usual variations, adaptations, modifications, deletions or additions of procedures and protocols described herein, and is within the scope of the following claims.

What is claimed is:

1. A method of deblocking an allylester, allyl carbonate, allyl carbamate or cinnamyl ester protecting group comprising the procedure of:
   reacting a compound having one or more said protecting groups, with a catalytic quantity of an organic insoluble polymer supported Pd(0) in a suitable organic solvent for said compound and in the presence of a nucleophile selected from the group consisting of 1,3-cyclopentanedione, 2-methyl-1,3-cyclopentanedione, 2-methyl-1,3-cyclohexanedione, potassium 2-ethylhexanoate and N-methyl morpholine, whereby said compound is deblocked;
   separating the reacted polymer supported Pd(0) from said deblocked compound: and
   regenerating the reacted polymer supported Pd(0) by reaction with more than one equivalent of a reducing agent in aqueous solution, where said reducing agent is $NaBH_4$.

2. The method of claim 1 wherein said polymer supported Pd(0) is a complex of polystyrene bound triphenylphosphine and tetrakistriphenylphosphine in a mole-to-mole ratio of between about 30:1 and about 50:1.

3. The method of claim 1 wherein said catalytic quantity of polymer supported Pd(0) is between about 30 mole % and about 0.25 mole % of said protecting group.

4. The method of claim 1 wherein said catalytic quantity of polymer-supported Pd(0) is between about 10 mole % and about 5 mole % of said protecting group.

5. The method of claim 1 wherein the compound is cefoxitin.

6. The method of claim 1 wherein the compound is imipenem.

7. A method of deblocking a protecting group with organic insoluble polymer supported Pd(0), and then regenerating the polymer supported Pd(0), comprising the steps of:
   (a) providing an equivalent of a compound having one or more protecting groups to be removed, said compound dissolved in an organic non-hydroxylic solvent, said protecting group selected from the group consisting of an allyl ester, allyl carbonate, allyl carbamate and cinnamyl ester;
   (b) adding about one equivalent of a necleophile;
   (c) mixing with about one equivalent of a polymer supported Pd(0) to yield deblocked compound and reacted polymer supported Pd(0);
   (d) separating the reacted polymer supported Pd(0) from deblocked compound; and
   (e) regenerating the reacted polymer supported Pd(0) by reaction with more than one equivalent of a reducing agent in aqueous solution.

8. The method of claim 7 wherein said nucleophile is selected from the group consisting of 1,3-cyclopentanedione, 2-methyl-1,3-cyclopentanedione, 2-methyl-1,3-cyclohexanedione, potassium 2-ethyl hexanoate, and N-methylmorpholine.

9. The method of of claim 7 wherein said reducing agent of step (e) is $NaBH_4$.

10. The method of claim 7 wherein step (d) is performed by adding aqueous solution, mixing, and removing the reacted polymer supported Pd(0) from the organic phase.

11. The method of claim 7 wherein the compound is cefoxitin.

12. The method of claim 1 wherein the compound is imipenem.

* * * * *